United States Patent [19]
Desbois et al.

[11] Patent Number: 4,575,571
[45] Date of Patent: Mar. 11, 1986

[54] PROCESS FOR THE SIMULTANEOUS HALOGENATION AND FLUORINATION OF AROMATIC DERIVATIVES

[75] Inventors: Michel Desbois, Rillieux; Camille Disdier, Lyons, both of France

[73] Assignee: Rhone-Poulenc Specialites Chimiques, France

[21] Appl. No.: 623,465

[22] Filed: Jun. 22, 1984

[30] Foreign Application Priority Data

Jun. 23, 1983 [FR]  France ................................ 83 10372

[51] Int. Cl.$^4$ ........................ C07C 17/12; C07C 17/20
[52] U.S. Cl. .................................... 570/140; 570/142; 570/145; 570/147; 570/164; 570/207; 570/208; 260/543 R; 568/74; 568/630; 568/639; 568/649; 568/656; 568/779; 568/937; 562/405; 558/425; 560/349
[58] Field of Search ............... 570/145, 147, 164, 207, 570/208, 141, 142, 140; 568/74, 656, 649, 630, 634, 779, 937; 562/405; 260/453 P, 465 G, 543 R

[56] References Cited

U.S. PATENT DOCUMENTS 2,881,224  4/1959  McCaulay ........................... 570/208
3,816,287  6/1974  Bockmann et al. ............. 204/163 R
3,966,832  6/1976  Lademann et al. ................. 570/145
4,061,688  12/1977  Maul et al. .......................... 570/145
4,367,350  1/1983  Hiramatsu et al. ................ 570/144
4,400,563  8/1983  Ohsaka et al. ..................... 570/144

FOREIGN PATENT DOCUMENTS 2375169  12/1977  France ................................ 570/144
2375168  7/1978  France ................................ 570/145
 955898  4/1964  United Kingdom .
1206389  9/1970  United Kingdom .

OTHER PUBLICATIONS

Houben-Weyl: "Methoden der Organischen Chemie," vol. V/3, Halogenverbindungen, 1962, pp. 678–681, Georg Thieme Verlag, Stuttgart, DE.

Primary Examiner—Thomas A. Waltz
Assistant Examiner—John A. Sopp
Attorney, Agent, or Firm—Finnegan, Henderson, Farabow, Garrett & Dunner

[57] ABSTRACT

A process for the stimulaneous halogenation and fluorination of aromatic derivatives substituted by at least one group containing a halogenoalkyl unit. The aromatic derivative is reacted with the halogen in liquid hydrofluoric acid. The products obtained are useful as intermediates for the synthesis of compounds having a plant-protecting or pharmaceutical activity.

12 Claims, No Drawings

PROCESS FOR THE SIMULTANEOUS HALOGENATION AND FLUORINATION OF AROMATIC DERIVATIVES

The present invention relates to a process for the simultaneous halogenation and fluorination of aromatic derivatives substituted by at least one group containing a halogenoalkyl unit. It relates more particularly to a process for the halogenation of the aromatic nucleus and a simultaneous process for the fluorination of the said group by halogen/fluorine exchange.

The term "halogenation of aromatic derivatives" is understood as meaning the attachment of at least one chlorine or bromine atom.

The term "aromatic derivatives substituted by at least one group containing a halogenoalkyl unit" is understood as meaning any monocyclic or polycyclic aromatic derivative corresponding to the following general formula:

$$Ar-(A-CX_1X_2Y)_n \qquad (I)$$

in which:

Ar represents a monocyclic or polycyclic aromatic radical which may contain at least one substituent other than $-(A-CX_1X_2Y)_n$, A represents a covalent bond, an oxygen atom or a sulfur atom, $X_1$ and $X_2$, which are identical or different, represent a halogen, Y corresponds to hydrogen, a halogen or an optionally halogenated alkyl chain having 1 to 3 carbon atoms, the halogens corresponding to $X_1$, $X_2$ and Y being identical or different, but at least one of them being other than fluorine, and n is equal to 1 or 2 and preferably equal to 1.

For greater clarity, the halogen/fluorine exchange of the group containing a halogenoalkyl unit will be designated by the term "fluorination-exchange".

It has been known for a long time to subject aromatic derivatives substituted by at least one group containing a halogenoalkyl unit to fluorination-exchange in a hydrofluoric acid medium, and then to chlorinate the aromatic derivative substituted by at least one group containing a fluoroalkyl unit, in a second, independent step, in the presence of a chlorination catalyst such as, in particular, FeCl$_3$, BF$_3$ (German Pat. No. 825,397) or Pt-on-alumina (German Pat. No. 1,034,609).

The fact that this is a two-step process has numerous disadvantages and, in particular, causes a loss of yield.

It has been possible, as described in Houben Weyl (volume 3, page 679), to carry out the chlorination and the fluorination-exchange in a single step using a catalyst such as antimony pentachloride in anhydrous hydrofluoric acid.

Those skilled in the art are very familiar with the properties of this catalyst, which behaves both as a chlorination catalyst and as a fluorination catalyst.

The process described above has the advantage of proceeding in a single step, but it requires the presence of a catalyst which cannot be recycled, and this presents problems of pollution from the technical point of view and problems of viability from the economic point of view.

The present invention, which overcomes the disadvantages of the prior art, relates to a single-step process for the halogenation and fluorination-exchange of aromatic compounds substituted by at least one group containing a halogenoalkyl unit, which comprises reacting the said aromatic compound with a halogen in liquid hydrofluoric acid. The hydrofluoric acid serves a dual purpose; it acts as a fluorinating agent for the substituent group on the nucleus and also acts as a solvent during the halogenation of the aromatic nucleus.

French Pat. No. 77/39,363, published under No. 2,375,169, which describes the preparation of perfluoroalkylbenzenes, is known in the prior art. In this process, the corresponding alkylbenzene is reacted with chlorine and hydrofluoric acid in the gas phase at high temperature. The temperature is generally between 350° and 600° C. It is specified in the said document that, above a certain temperature (generally above 450° C.), the fluorination reaction of the alkyl side-chain is accompanied by chlorination reactions of the benzene nucleus.

This chlorination reaction of the benzene nucleus thus appears to result from a parallel reaction involving the chlorine present in the medium, at a temperature above 450° C., the hydrofluoric acid not participating in the reaction. This is confirmed to those skilled in the art by East German Patent No. 15,100, which shows that, at high temperature, if chlorine is reacted with an alkylbenzene in the absence of hydrofluoric acid, derivatives chlorinated on the benzene nucleus are obtained in addition to the perchloroalkylbenzene. This is further confirmed by the analysis of this German patent in U.S. Pat. No. 3,816,287.

Thus, the prior art showed those skilled in the art that, to obtain the corresponding perfluoroalkylbenzene from an alkylbenzene, it was necessary to use on the one hand chlorine (at high temperature because the reaction was carried out without a catalyst), this chlorine giving secondary chlorination reactions on the nucleus in addition to the perchlorination reaction of the alkyl chain, and on the other hand hydrofluoric acid to replace the chlorine atoms of the perchloroalkyl chain with fluorine atoms.

By virtue of the present invention, which diverges very considerably from the interpretation acknowledged in the prior art, it has been possible to carry out the halogenation of an aromatic nucleus firstly without a catalyst and secondly without being obliged to use a high temperature.

These objectives are achieved by using a halogen in the presence of liquid hydrofluoric acid.

The present process can be used to halogenate the aromatic nucleus and exchange the halogens of the halogenoalkyl chain of any aromatic derivatives substituted by one or more groups containing a halogenoalkyl unit, irrespective of the other substituents present on the nucleus.

In fact, the aromatic nucleus can contain, for example, at least one halogen, hydroxyl group, nitro group, cyano group, isocyanate group, carboxyl group, alkyl or alkoxy group or phenyl or phenoxy group, in addition to the group containing a halogenoalkyl unit.

The halogen will be attached to the nucleus according to the substitution rules well known to those skilled in the art, as a function of the presence of ortho-, para- or meta-directing radicals.

The fluorination-exchange makes it possible to exchange the halogens of halogenomethyl, halogenomethoxy and halogenothiomethyl groups to give —CF$_3$, —OCF$_3$ and —SCF$_3$.

In the case of halogenoalkoxy and halogenothioalkyl groups, the exchange will take place on the carbon of the alkyl chain which is located in the α-position to the heteroatom.

Thus, the groups —OCCl$_2$—CCl$_3$ and —SCCl$_2$CCl$_3$ will be converted by fluorination-exchange to —OCF$_2$CCl$_3$ and —SCF$_2$CCl$_3$.

On the other hand, the halogen atoms directly attached to the benzene nucleus are not affected by the fluorination-exchange.

The hydrofluoric acid used for the present invention is preferably anhydrous hydrofluoric acid.

The molar ratio of the hydrofluoric acid to the starting aromatic compound is preferably between 10 and 100. An appreciably larger quantity does not have an adverse effect on the invention.

The quantity of halogen used is fixed by those skilled in the art, taking into account whether the desired product corresponds to monohalogenation of polyhalogenation. For monohalogenation, the reaction is preferably carried out in the presence of a stoichiometric deficit of halogen, that is to say with a molar ratio of halogen to aromatic compound preferably of between 0.5 and 0.9. For polyhalogenation, it is preferred to carry out the reaction with an excess of halogen. The halogen can be employed in a sealed enclosure under autogenous pressure (generally 1 to 50 bar) or under atmospheric pressure, by bubbling, or in any other device known to those skilled in the art.

The temperature at which the reaction is carried out is preferably between −20° C. and 150° C.

If the temperature is to be above 20° C., the reaction will have to take place under pressure because the hydrofluoric acid must be liquid.

The reaction time varies from a few minutes to a few hours.

This reaction time varies with the number of halogen atoms which it is desired to attach to the nucleus, and also with the starting materials and the reaction temperature.

The final halogenated aromatic product is isolated, for example by distillation of the hydrofluoric acid, which can thus be recovered and recycled, this being an important advantage of the process of the invention. It can also be isolated by extraction with organic solvents well known to those skilled in the art.

Examples of products of the formula (I) which may be mentioned are: trichloromethylbenzene, metabistrichloromethylbenzene, trichloromethoxybenzene, parabistrichloromethoxybenzene, trichloromethylthiobenzene, chlorotrichloromethylbenzenes, fluorotrichloromethylbenzenes, dichlorobromomethylbenzene, tribromomethylbenzene, chlorotrichloromethoxybenzenes, fluorotrichloromethoxybenzenes, p-trichloromethylphenyl isocyanate, p-trichloromethylphenyl chloroformate, pentachloroethoxybenzene, pentachloroethylthiobenzene, paratrichloromethylphenol and 2-chloro-4-trichloromethylphenol.

Although the invention is not limited to these compounds, it has a particularly advantageous application in the halogenation and the fluorination-exchange of perchloroalkyl, perchloroalkoxy and perchlorothioalkyl aromatic derivatives such as, for example, trichloromethylbenzenes, trichloromethoxybenzenes and trichloromethylthiobenzenes.

The halogenated aromatic derivatives substituted by a fluoroalkyl group are used as synthesis intermediates in the pharmaceutical and plant protection industries.

The present invention will be understood more easily with the aid of the examples which follow, which are given by way of indication but without in any way implying a limitation.

EXAMPLE 1

50 ml (2.5 mol) of anhydrous hydrofluoric acid and 9.8 g (0.05 mol) of trichloromethylbenzene are introduced into a 250 ml reactor equipped with a magnetic stirrer bar and cooled to about 0° C. The reaction mixture is left to degas (evolution of hydrochloric acid) for one hour, with stirring, and the reactor is then closed and brought to a pressure of 5.5 bar (at 20° C.) with chlorine gas. The whole is then heated at 90° C. for 4 hours, with stirring. After cooling to about 0° C. again, the reactor is decompressed and the crude reaction mixture obtained is introduced onto 110 g of crushed ice. The heterogeneous mixture resulting from this treatment is extracted with 300 cm$^3$ of methylene chloride.

After decantation, the organic phases are combined.

The combined organic phases are washed 2 times with 100 cm$^3$ of softened water and dried. Analyses carried out by gas chromatography (% area), IR spectrometry and mass spectrometry give the following result:

| | |
|---|---|
| trifluoromethylbenzene: | 26.8% |
| m-chlorotrifluoromethylbenzene: | 48.1% |
| other chlorotrifluoromethylbenzenes: | 25.1% |

EXAMPLE 2

The procedure is identical to that of Example 1, the compounds and conditions being those given below and the treatment of the crude reaction mixture with ice being replaced with extraction of this crude mixture 2 times using 100 cm$^3$ of carbon tetrachloride, these organic phases subsequently being treated in the normal way.

| | |
|---|---|
| Anhydrous hydrofluoric acid: | 100 g (5 mol) |
| p-Fluorotrichloromethylbenzene: | 10.7 g (0.05 mol) |
| Temperature: | 80° C. |
| Chlorine pressure: | 4 bar at 20° C. |
| Duration: | 21 hours |

Analyses carried out by gas chromatography (% area), IR spectrometry and mass spectrometry give the following result:

| | |
|---|---|
| p-fluorotrifluoromethylbenzene: | 58.6% |
| 4-fluoro-3-chlorotrifluoromethylbenzene: | 24.6% |

EXAMPLE 3

The procedure is identical to that of Example 1, the compounds and conditions being as follows:

| | |
|---|---|
| Anhydrous hydrofluoric acid: | 100 g (5 mol) |
| p-Trichloromethylphenyl isocyanate: | 23.6 g (0.1 mol) |
| Temperature: | 20° C. |
| Chlorine pressure: | 4 bar at 20° C. |
| Duration: | 20 hours 25 minutes |

Analyses carried out by gas chromatography (% area), IR spectrometry and mass spectrometry give the following result:

| | |
|---|---|
| carbamoyl fluoride of 4-trifluoromethyl-2-chloroaniline: | 81% |

EXAMPLE 4

The procedure is identical to that of Example 1, the compounds and conditions being those given below and the treatment of the crude reaction mixture with ice being replaced with distillation of this crude mixture up to a bottom temperature of 80° C., under atmospheric pressure, in order to remove as much of the hydrofluoric acid solvent as possible.

| | |
|---|---|
| Anhydrous hydrofluoric acid: | 100 g (5 mol) |
| Trichloromethoxybenzene: | 10.6 g (0.05 mol) |
| Temperature: | 120° C. |
| Chlorine pressure: | 4 bar at 20° C. |
| Duration: | 3 hours |

Analyses carried out by gas chromatography (% area), IR spectrometry and mass spectrometry give the following result:

| | |
|---|---|
| p-chlorotrifluoromethoxybenzene: | 53% |
| dichlorotrifluoromethoxybenzene: | 15% |

EXAMPLE 5

The procedure is identical to that of Example 1, the compounds and conditions being as follows:

| | |
|---|---|
| Anhydrous hydrofluoric acid: | 100 g (5 mol) |
| p-Chlorotrichloromethoxybenzene: | 12.3 g (0.05 mol) |
| Temperature: | 150° C. |
| Chlorine pressure: | 4 bar at 20° C. |
| Duration: | 3 hours 30 minutes |

Analyses carried out by gas chromatography (% area), IR spectrometry and mass spectrometry give the following result

| | |
|---|---|
| p-chlorotrifluoromethoxybenzene: | 19% |
| 2,4-dichlorotrifluoromethoxybenzene: | 28.3% |
| trichlorotrifluoromethoxybenzene: | 12.5% |

EXAMPLE 6

The procedure is identical to that of Example 1, the chlorine being replaced with bromine and the compounds and conditions being as follows:

| | |
|---|---|
| Anhydrous hydrofluoric acid: | 100 g (5 mol) |
| Trichloromethylbenzene: | 19.5 g (0.1 mol) |
| Temperature: | 100° C. |
| Bromine: | 16 g (0.1 mol) |
| Duration: | 24 hours |

Analyses carried out by gas chromatography (% area) IR spectrometry and mass spectrometry give the following result:

| | |
|---|---|
| trifluoromethylbenzene: | 36.4% |
| m-bromotrifluoromethylbenzene: | 57.7% |

EXAMPLE 7

The procedure is identical to that of Example 1, the chlorine being replaced with bromine and the compounds and conditions being as follows:

| | |
|---|---|
| Anhydrous hydrofluoric acid: | 50 g (2.5 mol) |
| Trichloromethylthiobenzene: | 11.3 g (0.05 mol) |
| Temperature: | 100° C. |
| Bromine: | 8 g (0.05 mol) |
| Duration: | 3 hours 40 minutes |

Analyses carried out by gas chromatography (% area), IR spectrometry and mass spectrometry give the following result:

| | |
|---|---|
| trifluoromethylthiobenzene: | 28% |
| p-bromotrifluoromethylthiobenzene: | 53.1% |
| o-bromotrifluoromethylthiobenzene: | 14.9% |

EXAMPLE 8

The procedure is identical to that of Example 1, the chlorine being replaced with bromine and the compounds and conditions being as follows:

| | |
|---|---|
| Anhydrous hydrofluoric acid: | 100 g (5 mol) |
| Trichloromethoxybenzene: | 21.2 g (0.1 mol) |
| Temperature: | 120° C. |
| Bromine: | 16 g (0.1 mol) |
| Duration: | 3 hours 40 minutes |

Analyses carried out by gas chromatography (% area), IR spectrometry and mass spectrometry give the following result:

| | |
|---|---|
| trifluoromethoxybenzene: | 14.1% |
| monobromotrifluoromethoxybenzene: | 55.6% |

EXAMPLE 9

The procedure is identical to that of Example 1, except that the reaction is carried out at atmospheric pressure and the chlorine is introduced by being bubbled into the reaction medium, the compounds and conditions being as follows:

| | |
|---|---|
| Anhydrous hydrofluoric acid: | 40 g (2 mol) |
| p-Trichloromethylphenyl isocyanate: | 47.2 g (0.2 mol) |
| Temperature: | 10° C. |
| Chlorine pressure: | atmospheric pressure |
| Duration: | 5 hours |

Analyses carried out by gas chromatography (% area), IR spectometry and mass spectrometry give the following result:

| | |
|---|---|
| carbamoyl fluoride of 4-trifluoromethyl-2-chloroaniline: | 73% |

EXAMPLE 10

The procedure is identical to that of Example 1, the compounds and conditions being as follows:

| | |
|---|---|
| Anhydrous hydrofluoric acid: | 100 g (5 mol) |
| p-Chlorotrichloromethylbenzene: | 23 g (0.1 mol) |
| Temperature: | 100° C. |
| Chlorine pressure: | 4 bar at 20° C. |
| Duration: | 18 hours |

Analyses carried out by gas chromatography (% area), IR spectrometry and mass spectrometry give the following result:

| | |
|---|---|
| p-chlorotrifluoromethylbenzene: | 21% |
| 3,4-dichlorotrifluoromethylbenzene: | 74% |
| other chlorotrifluoromethylbenzenes: | 5% |

EXAMPLE 11

The procedure is identical to that of Example 1, the compounds and conditions being as follows:

| | |
|---|---|
| Anhydrous hydrofluoric acid: | 100 g (5 mol) |
| p-Bistrichloromethoxybenzene: | 17.25 g (0.05 mol) |
| Temperature: | 150° C. |
| Chlorine pressure: | 4 bar at 20° C. |
| Duration: | 4 hours |

Analyses carried out by gas chromatography (% area), IR spectrometry and mass spectrometry give the following result:

| | |
|---|---|
| p-bistrifluoromethoxybenzene: | 42% |
| monochloro-p-bistrifluoromethoxybenzene: | 14% |
| dichloro-p-bistrifluoromethoxybenzene: | 6% |

EXAMPLE 12

The procedure is identical to that of Example 1, the compounds and conditions being as follows:

| | |
|---|---|
| Anhydrous hydrofluoric acid: | 50 g (2.5 mol) |
| p-Trichloromethylphenyl chloroformate: | 13.7 g (0.05 mol) |
| Temperature: | 80° C. |
| Chlorine pressure: | 4 bar at 20° C. |
| Duration: | 4 hours 30 minutes |

Analyses carried out by gas chromatography (% area), IR spectrometry and mass spectrometry give the following result:

| | |
|---|---|
| p-trifluoromethylphenyl fluoroformate: | 70% |
| 2-chloro-4-trifluoromethylphenyl fluoroformate: | 1.5% |

EXAMPLE 13

The procedure is identical to that of Example 1, the compounds and conditions being as follows:

| | |
|---|---|
| Anhydrous hydrofluoric acid: | 50 g (2.5 mol) |
| 2-Chloro-4-trichloromethylphenol: | 9.8 g (0.05 mol) |

-continued

| | |
|---|---|
| Temperature: | 100° C. |
| Chlorine pressure: | 3 bar at 20° C. |
| Duration: | 4 hours |

Analyses carried out by gas chromatography (% area), IR spectrometry and mass spectrometry give the following result:

| | |
|---|---|
| 2,6-dichlorotrifluoromethylphenol and 2,5-dichlorotrifluoromethylphenol: | 75% |
| trichlorotrifluoromethylphenol: | 13%. |

What is claimed is:

1. A process for the halogenation and fluorination of an aromatic derivative substituted by at least one group containing a halogenoalkyl unit comprising the step of reacting, in the substantial absence of a halogenation catalyst other than liquid hydrofluoric acid, (a) an aromatic derivative substituted by at least one group containing a halogenoalkyl unit corresponding to the formula:

$$Ar-(A-CX_1X_2Y)_n$$

in which:

Ar is a monocyclic or polycyclic aromatic radical which may contain at least one substituent other than $-(A-CX_1X_2Y)_n$, A is a covalent bond, oxygen or sulfur, $X_1$ and $X_2$, which are identical or different, are a halogen, Y is selected from the group consisting of hydrogen, a halogen and an optionally halogenated alkyl chain having 1 to 3 carbon atoms; and wherein the halogens corresponding to $X_1$, $X_2$ and Y are identical or different, but at least one of them is other than fluorine; and n is equal to 1 or 2; with (b) a halogen in liquid hydrofluoric acid for a time sufficient to effect halogenation of the aromatic ring of said aromatic derivative and to effect halogen/fluorine exchange on said group containing a halogenoalkyl unit.

2. The process of claim 1, wherein n is equal to 1.

3. The process of claim 1, wherein the halogen to be reacted with said aromatic derivative is selected from the group consisting of chlorine and bromine.

4. The process of claim 1, wherein the hydrofluoric acid is anhydrous.

5. The process of claim 1, wherein the molar ratio of hydrofluoric acid to aromatic derivative ranges from 10 to 100.

6. The process of claim 5, wherein the molar ratio ranges from 50 to 100.

7. The process of claim 1, wherein the halogenation and the halogen/fluorine exchange are carried out at from −20° to 150° C.

8. The process of claim 1, wherein the aromatic derivative is selected from the group consisting of perchloroalkyl, perchloroalkoxy and perchlorothioalkyl derivatives.

9. The process of claim 8, wherein the aromatic derivative is selected from the group consisting of trichloromethylbenzenes, trichloromethoxybenzenes and trichloromethylthiobenzenes.

10. The process of claim 1, wherein said Ar monocyclic or polycyclic aromatic radical contains, in addition to the $-(A-CX_1X_2Y)_n$ substituent, at least one substituent selected from the group consisting of halogen, hydroxyl, nitro, cyano, isocyanate, carboxyl, chloroformate, alkyl, alkoxy, phenyl and phenoxy.

11. The process of claim 10, wherein said at least one substituent is selected from the group consisting of fluorine, isocyanate, chlorine, and hydroxyl.

12. The process of claim 11, wherein said at least one substituent is chlorine.

* * * * *